United States Patent
Cunningham

(10) Patent No.: US 6,646,270 B2
(45) Date of Patent: Nov. 11, 2003

(54) GERMICIDAL MAILBOX

(76) Inventor: John R. Cunningham, 140 Coco Plum Dr., #4, Marathon, FL (US) 33050

( * ) Notice: Subject to any disclaimer, the term of this patent is extended or adjusted under 35 U.S.C. 154(b) by 0 days.

(21) Appl. No.: 10/326,198

(22) Filed: Dec. 20, 2002

(65) Prior Publication Data

US 2003/0136919 A1 Jul. 24, 2003

Related U.S. Application Data

(60) Provisional application No. 60/342,593, filed on Dec. 20, 2001.

(51) Int. Cl.[7] .............................. H01J 37/20; A61L 2/10
(52) U.S. Cl. .............................. 250/455.11; 250/504 R; 250/492.1; 422/24; 422/22
(58) Field of Search ...................... 250/455.11, 454.11, 250/453.11, 504 R, 492.1, 493.1; 232/35; 422/24, 186.3; 312/209

(56) References Cited

U.S. PATENT DOCUMENTS

| | | | | |
|---|---|---|---|---|
| 4,520,932 A | * | 6/1985 | Matsuda et al. ............ | 209/545 |
| 5,419,557 A | * | 5/1995 | Kirkland et al. ......... | 273/144 B |
| 5,688,475 A | * | 11/1997 | Duthie, Jr. ................ | 422/186.3 |
| 6,461,568 B1 | * | 10/2002 | Eckhardt ................ | 250/455.11 |
| 2003/0085266 A1 | * | 5/2003 | Simon .......................... | 232/37 |
| 2003/0086821 A1 | * | 5/2003 | Mattews ....................... | 422/29 |

* cited by examiner

Primary Examiner—John R. Lee
Assistant Examiner—James P. Hughes
(74) Attorney, Agent, or Firm—Akerman Senterfitt; Michael C. Cesarano

(57) ABSTRACT

A germicidal mailbox receives mail in an internal, rotatable cage, and tumbles such mail while irradiating it with ultraviolet light at a wavelength of 254 nanometers to kill or render inert microbes on the mail that could carry diseases to which humans are susceptible. After the mail has been tumbled and irradiated, it is safe for handling by humans without the danger of infection and disease from microbes that may purposefully, through terrorism, or accidentally have become attached to the mail.

12 Claims, 2 Drawing Sheets

GERMICIDAL MAILBOX

This application claims the benefit of Provisional Application No. 60/342,573, filed Dec. 20, 2001.

BACKGROUND OF THE INVENTION

It has become known that dangerous micro organisms can be transmitted and distributed through the mail of many countries' postal services. This method of transmitting deadly microbes, particularly anthrax, has become popular with terrorists and others who seek to spread death and disease throughout a population. Although virulent strains of microbes clearly become deadly when the packages in which they are wrapped or sealed are opened, there is an increasing recognition that the risk of infection through secondary transmission due to microbes contaminating the outside of packages is very high where mail has traversed through a mail facility that was previously exposed to deadly microbes.

SUMMARY OF THE INVENTION

This invention prevents infection due to secondary transmission by thoroughly cleansing the external surfaces of letters, magazines, and other items of mail prior to their being touched by the intended addressees. According to the invention, such cleansing will take place in the addressee's local mailbox between the time it is delivered by the postal service and the time the addressee opens the mailbox to retrieve the mail. Cleaning of items of mail is accomplished by irradiating all exposed surfaces of an item of mail with ultraviolet light at a wavelength of 254 nanometers. This frequency of light has a germicidal effect upon exposed microbes and, if they are exposed for a sufficient length of time, will be effective to render them harmless.

According to the invention, a wire cage or basket is fitted within a standard mailbox, such as it commonly used for home delivery. This style of mailbox has a flat, rectangular floor at the bottom, sides that rise straight, vertically from the longitudinal sides of the floor up to a distance of about 8"–9", and then are rounded to meet at the top to form a semicircular upper portion. The rear wall is flat, and shaped like an inverted "U" while there is a door having a similar shape at the front. The door is hinged at the bottom, and opens from the top downward to expose the interior. An ultraviolet lamp providing light at a wavelength of 254 nanometers is located lengthwise at the top of the mailbox. A cylindrical wire basket or cage is enclosed lengthwise within the mailbox, and may or may not be open at the front end. A motor and a timing circuit that may include a microprocessor occupy the extreme rear portion of the mailbox, and the motor is attached to the wire, cylindrical basket, through a gearing arrangement if necessary, to cause the basket to rotate about its longitudinal axis. This rotation causes items of mail placed within the basket to tumble, such that all exposed surfaces will eventually be exposed to the ultraviolet light. A magnetic switch is located at the front opening of the mailbox, and is tripped "on" whenever the door is closed. The timing circuit controls both the ultraviolet light and the motor, and causes them to become activated whenever the magnetic switch initiates a closure. A preprogrammed timer operates the ultraviolet lamp and the motor for a predetermined length of time, that will be approximately 15 minutes for most purposes, and then shuts off the lamp and motor. The unit is attached to a constant electrical source, and will automatically activate whenever the mailbox door is opened and then closed.

DETAILED DESCRIPTION OF THE PREFERRED EMBODIMENTS

Figure 1:
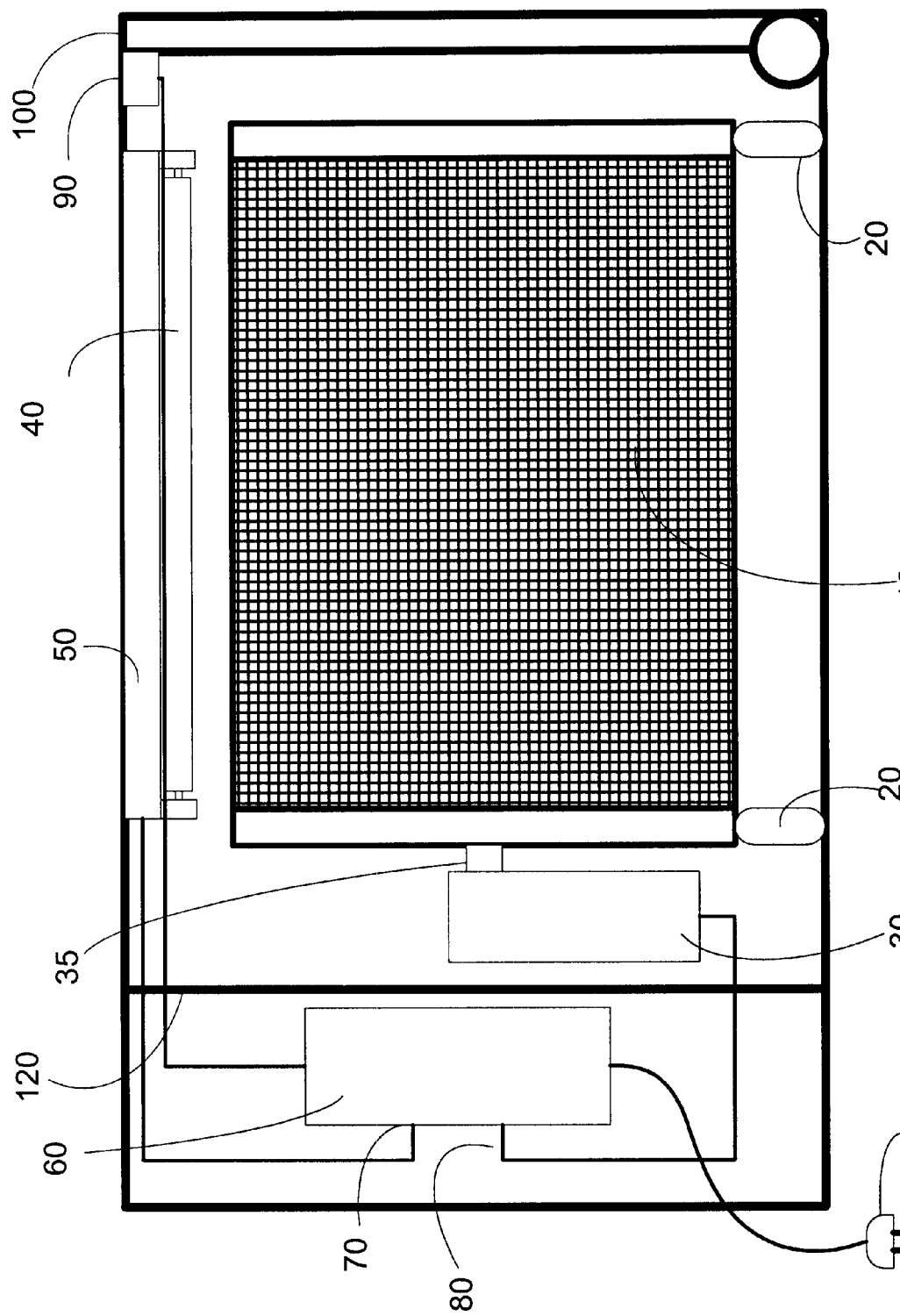
FIG. 1 depicts a sideview of the apparatus of this invention as though a sidewall were not present.

FIG. 1 shows the interior of the mailbox of this invention. A cylindrical wire cage or basket 10 is supported by rollers 20 located at either end of the wire cage. An electric motor 30 and any associated gear reduction apparatus is located at the rear of the mailbox behind the basket. A shaft 35 from the motor is attached to the wire basket and causes the basket to turn when the motor is actuated.

In FIG. 1, a timer and microprocessor are built into a printed circuit board 60 also located at the rear of the mailbox. The printed circuit board is separated from the motor by a weatherproof panel 120. Power is supplied to the circuit board through a conventional electrical connection 110. One plug 80 from the circuit board provides power to the electric motor 30, while a second plug 70 provides power to an ultraviolet lamb fixture 50 which supports an ultraviolet lamp 40.

A magnetic switch 90 is located at the front of the mailbox, and is actuated to complete a closed circuit whenever the mailbox door 100 is closed. The timer and microprocessor are programmed so that a predetermined timing sequence is initiated whenever the mailbox door is opened for more than approximately two (2) seconds, and is then closed. Upon the commencement of a timing sequence, the printed circuit board 60 will provide power to actuate the motor 30, and power to energize the ultraviolet lamp 40. The ultraviolet lamp will provide ultraviolet light at a frequency of 254 nanometers, which is a frequency that is appropriate to kill microbes that are exposed to the light. The motor causes the wire basket 10 to rotate, and any items of mail that are in the basket will be tumbled. The tumbling action results in all external surfaces of mailed items to be exposed to the ultraviolet light, and after a period of exposure, any dangerous microbes are rendered inert or dead. Preferably a treatment time of 15 minutes is sufficient to assure that any deadly microbes have been killed. In some embodiments, the effectiveness of the ultraviolet action may be enhanced by applying ultraviolet rays in pulses, rather than through a constant exposure. If the tumbling sequence should be interrupted, either through a power loss or through the reopening the mailbox door, the sequence will be reinitiated for another timing sequence.

Figure 2:
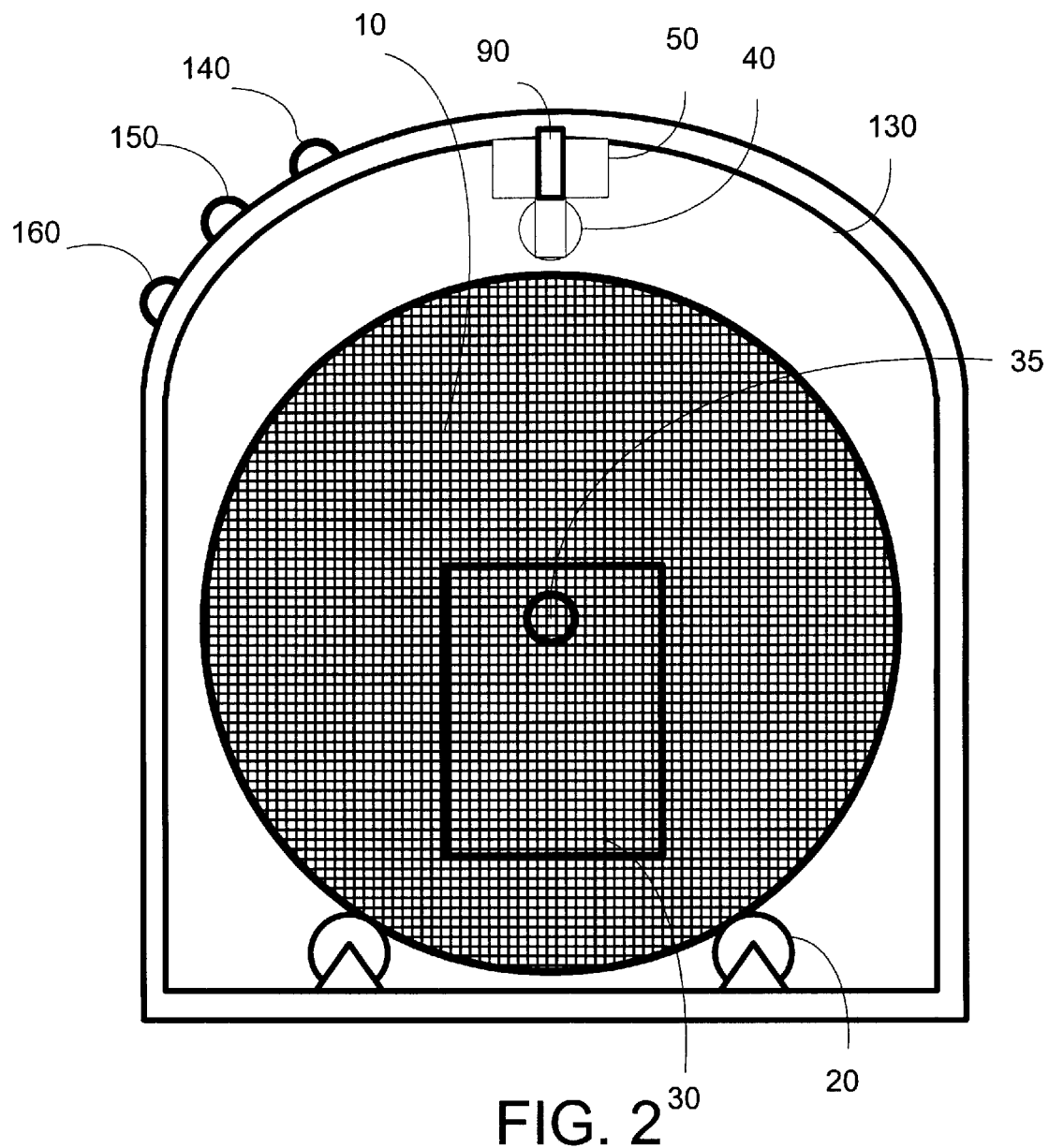
FIG. 2 depicts the apparatus of this invention from a front view with the mailbox door open (or not visible).

In FIG. 2 it may be seen that wire basket 10 is supported by rollers 20 on either side of the basket as well as at the front and back, for a total of four rollers. Magnetic switch 90 is located at the top of the mailbox, and electric motor 30 and its shaft 35 may be seen at the rear of the mailbox. The inner surfaces of the sidewalls of the mailbox 130 may be coated with a reflective coating to reflect ultraviolet light and enhance the action of the light in acting as a germicide against virus, bacteria, and mold spores.

In a preferred embodiment, a sequence of lights may be visibly mounted on the mailbox to indicate that power is present 140, that a tumbling sequence is taking place 150, or that a tumbling sequence has been completed 160. Power and sequencing for the lights will be provided by the microprocessor.

Following the completion of a cleansing cycle, items in the wire basket may safely be removed without danger of contamination on their external surfaces.

I claim:

1. A germicidal mailbox comprising:

an outer housing, said outer housing being opaque to ultraviolet light and having one or more access doors;

said outer housing enclosing an interior cage, said cage being at least large enough to receive articles of mail of standard sizes, said cage being rotatable along a longitudinal axis;

an electric motor electrically connected to a first circuit and being in series with a first switch, and having a physical interconnection to said cage for rotating said cage when said motor and said first circuit are activated by closing said first switch;

an ultraviolet lamp located within said housing and outside of said cage, said lamp being electrically connected to a second circuit being in series with a second switch, said lamp being physically situated to irradiate the interior of said cage when said second circuit is actuated by closing said second switch;

said first switch becoming closed upon the occurrence of a first predetermined event, and said second switch becoming closed upon the occurrence of a second predetermined event;

said lamp, when activated for a predetermined length of time, radiating ultraviolet light at a wavelength sufficient to render microbes located on articles of mail situated within said cage incapable of transmitting disease to humans;

a power source connected to said first and second circuits such that, when said first and second switches are closed, said cage will rotate and articles of mail contained within said cage will tumble, and said lamp will radiate ultraviolet light sufficient to render microbes within said cage harmless.

2. A germicidal mailbox as claimed in claim 1, further comprising a reflective interior surface of said housing such that ultraviolet radiation will be substantially reflected from the interior surfaces of said housing.

3. A germicidal mailbox as claimed in claim 1, further comprising one or more rollers situated within said housing to support said cage while said cage is rotating.

4. A germicidal mailbox as claimed in claim 1, wherein said ultraviolet lamp produces radiation at a wavelength of approximately 254 nanometers.

5. A germicidal mailbox as claimed in claim 1, further comprising a timer, said timer causing said first switch and said second switch to close upon the occurrence of said first predetermined event and causing said first switch and said second switch to open upon the expiration of a predetermined length of time.

6. A germicidal mailbox as claimed in claim 5 further comprising one or more third switches, each said third switch corresponding and being physically connected to one of said one or more access doors, each said third switch being closed when said access door corresponding to said third switch is closed.

7. A germicidal mailbox as claimed in claim 6 further comprising one or more indicator lights visible from outside said housing, said one or more lights indicating the presence of electrical power, the operation of said ultraviolet lamp or the operation of said electric motor.

8. A germicidal mailbox comprising:

an outer container having one or more access doors, said outer container substantially enclosing an ultraviolet lamp such that ultraviolet radiation produced by said lamp is confined within said outer container when said one or more access doors are closed;

a rotatable mesh container that is large enough to receive and tumble articles of standard size mail when rotated;

an electric motor having a shaft mechanically interconnected to said mesh container;

an electrical circuit having a power source, said ultraviolet lamp and said electric motor being connected to said circuit and being actuated by at least a first switch and one or more second switches;

said one or more second switches being proximate to and corresponding to said one or more access door and configured to allow said electric motor and said ultraviolet lamp to operate only when said one or more access doors are closed;

such that articles of mail contained within said mesh container will be tumbled and irradiated with ultraviolet radiation when said access door is closed and said first switch is closed.

9. A germicidal mailbox as claimed in claim 8 wherein said ultraviolet lamp produces radiation at a wavelength of approximately 254 nanometers.

10. A germicidal mailbox as claimed in claim 8, further comprising a timer connected to said first switch whereby, when said timer commences a timing sequence and said one or more access doors are closed, said first switch will close and cause said electric motor and said ultraviolet lamp to operate, and when said timing sequence has completed, said timer will cause said first switch to open, and said electric motor and said ultraviolet lamp will cease operating.

11. A germicidal mailbox as claimed in claim 10 further comprising one or more indicator lights connected to said electrical circuit whereby said indicator lights will provide the immediate operational status of said electrical motor and said ultraviolet lamp.

12. A germicidal mailbox as claimed in claim 10, said electrical circuit further comprising a delay circuit and a third switch, said third switch actuating said delay circuit to cause said electric motor and said ultraviolet lamp to operate only after a predetermined length of time has passed since said third switch was actuated, and said timer causing said electric motor and said ultraviolet lamp to cease operating after the passage of a predetermined length of time.

* * * * *